United States Patent
Kim et al.

(10) Patent No.: US 8,227,095 B2
(45) Date of Patent: Jul. 24, 2012

(54) ORGANIC COMPOUND AND ORGANIC LIGHT EMITTING DEVICE CONTAINING THE SAME

(75) Inventors: Myeong-Suk Kim, Hwaseong-si (KR); Byoung-Ki Choi, Hwaseong-si (KR); Dong-woo Shin, Seoul (KR); O-Hyun Kwon, Seoul (KR); Haa-Jin Yang, Yongin-si (KR); Bong-Jin Moon, Goyang-si (KR); Myoung-Soo Ham, Samcheok-si (KR)

(73) Assignees: Samsung Electronics Co., Ltd., Suwon-si (KR); Industry-University Cooperation Foundation Sogang University, Seoul (KR)

( * ) Notice: Subject to any disclaimer, the term of this patent is extended or adjusted under 35 U.S.C. 154(b) by 383 days.

(21) Appl. No.: 12/557,047

(22) Filed: Sep. 10, 2009

(65) Prior Publication Data

US 2010/0148158 A1 Jun. 17, 2010

(30) Foreign Application Priority Data

Dec. 16, 2008 (KR) ........................ 10-2008-0127836

(51) Int. Cl.
*H01L 51/54* (2006.01)
*C07C 13/465* (2006.01)
*C07C 2/86* (2006.01)

(52) U.S. Cl. ........ 428/690; 428/917; 313/504; 313/506; 257/40; 585/27; 585/320

(58) Field of Classification Search ........................ None
See application file for complete search history.

(56) References Cited

U.S. PATENT DOCUMENTS

2008/0145708 A1* 6/2008 Heil et al. ..................... 428/704
(Continued)

FOREIGN PATENT DOCUMENTS

JP 2003-203779 7/2003
(Continued)

OTHER PUBLICATIONS

Soobshcheniia Akademii Nauk Gruzinskoi SSR, 1987; 127(3), pp. 537-540.*

(Continued)

*Primary Examiner* — Dawn L. Garrett
(74) *Attorney, Agent, or Firm* — H.C. Park & Associates, PLC

(57) ABSTRACT

Disclosed is a compound represented by the following Formula 1:

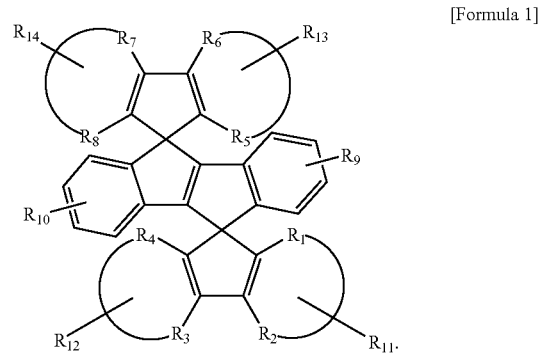

[Formula 1]

The compound exhibits improved solubility and thermal stability in an organic light emitting device. An organic light emitting device including the compound, improves the driving voltage, the emission efficiency, and the color purity of an organic light emitting display.

21 Claims, 5 Drawing Sheets

U.S. PATENT DOCUMENTS

| | | | |
|---|---|---|---|
| 2008/0206447 A1 | 8/2008 | Inoue et al. | |
| 2008/0220285 A1* | 9/2008 | Vestweber et al. | 428/690 |
| 2009/0189519 A1* | 7/2009 | Lee et al. | 313/504 |

FOREIGN PATENT DOCUMENTS

| | | |
|---|---|---|
| JP | 2005-179488 | 7/2005 |
| JP | 2006-219393 | 8/2006 |
| JP | 2008-050529 | 3/2008 |
| KR | 10-2005-0116279 | 12/2005 |
| KR | 10-2006-0025933 | 3/2006 |
| KR | 10-0718103 | 5/2007 |
| KR | 10-0767571 | 10/2007 |
| KR | 10-2008-0039763 | 5/2008 |
| KR | 10-2008-0047209 | 5/2008 |
| KR | 10-2008-0049770 | 6/2008 |
| KR | 10-2008-0067338 | 7/2008 |

OTHER PUBLICATIONS

Soobshcheniia Akademii Nauk Gruzinskoi SSR, 1988, 129(3), pp. 553-556.*

* cited by examiner

ORGANIC COMPOUND AND ORGANIC LIGHT EMITTING DEVICE CONTAINING THE SAME

CROSS REFERENCE TO RELATED APPLICATION

This application claims priority from and the benefit of Korean Patent Application No. 10-2008-0127836, filed on Dec. 16, 2008, which is hereby incorporated by reference for all purposes as if fully set forth herein.

BACKGROUND OF THE INVENTION

1. Field of the Invention

Aspects of the present disclosure relate to an organic compound, and an organic light emitting device containing the same.

2. Discussion of the Background

An organic light emitting device has two electrodes, and an organic emissive layer interposed between the two electrodes. In operation, electrons and holes from the two electrodes are injected into the organic emissive layer to generate excitons pursuant to the bonds of the electrons and the holes, and when the excitons shift from the excited state to the ground state, light is emitted, thereby displaying images.

Meanwhile, as an organic light emitting display with the organic light emitting device has an emissive characteristic and does not require a separate light source, the organic light emitting display may be advantageous in terms of power consumption, response time, viewing angle, and contrast ratio compared to other types of displays.

In addition to the organic emissive layer, the organic light emitting device may have an auxiliary layer to enhance the light emitting efficiency of the organic emissive layer. The driving voltage, emission efficiency, and life span of the organic light emitting display depend upon the compounds used for the organic emissive layer and the auxiliary layer, accordingly, extensive studies regarding such compounds have been undertaken.

SUMMARY OF THE INVENTION

Exemplary embodiments of the present invention provide an organic compound that has excellent solubility and thermal stability.

Exemplary embodiments of the present invention also provide an organic light emitting element based on the organic compound, the organic light emitting element has enhanced driving voltage, emission efficiency, and color purity.

Exemplary embodiments of the present invention also provide a light emitting display comprising the organic light emitting element.

Additional features of the invention will be set forth in the description which follows, and in part will be apparent from the description, or may be learned by practice of the invention.

An exemplary embodiment of the present invention discloses a compound represented by Formula 1.

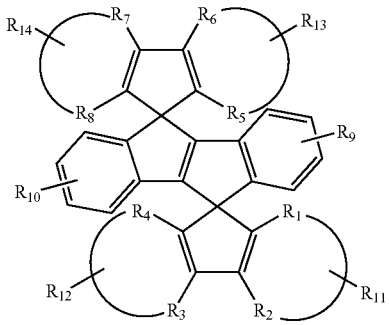

[Formula 1]

In Formula 1, wherein each of $R_1$ and $R_2$, $R_3$ and $R_4$, $R_5$ and $R_6$, and $R_7$ and $R_8$ independently represents a 5 or 6-membered cyclic or linear substituent, and each of $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —N($Z_1$)($Z_2$), or —Si($Z_3$)($Z_4$)($Z_5$), where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

An exemplary embodiment of the present invention also discloses a method of manufacturing a compound, which includes reacting a compound represented by Formula 2 with an organic metal compound in an organic solvent to form a first mixture, mixing a compound represented by Formula 3 with the first mixture to form a second mixture, and reacting the second mixture under an acid catalyst to form a compound represented by Formula 1.

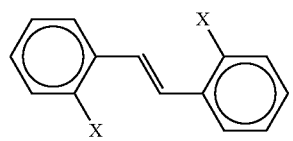

[Formula 2]

In Formula 2, X represents F, Br, or Cl.

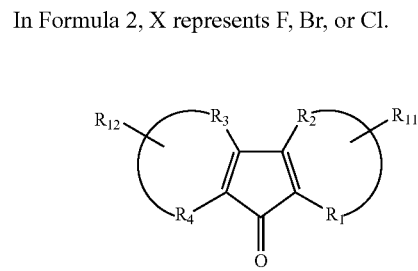

[Formula 3]

An exemplary embodiment of the present invention also discloses a method of manufacturing a compound, which includes preparing a compound represented by Formula 5, reacting the compound represented by Formula 5 with benzaldehyde and halogenating the reacted compound to form a third mixture, reacting the third mixture with an organic metal compound in an organic solvent to form a fourth mixture, and reacting the fourth mixture under an acid catalyst to form a compound represented by Formula 1.

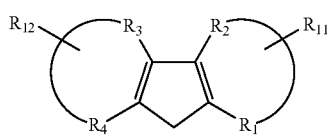

[Formula 5]

An exemplary embodiment of the present invention also discloses an organic light emitting device, which comprises an anode disposed on a substrate. A hole transport layer is disposed on the anode, an emission layer is disposed on the hole transport layer and the emission layer contains a compound represented by Formula 1. An electron transport layer is disposed on the emission layer, and a cathode is disposed on the electron transport layer.

An exemplary embodiment of the present invention also discloses an organic light emitting display comprising a first signal line and a second signal line crossing each other, a switching thin film transistor connected to the first and second signal lines, and a driving thin film transistor connected to the switching thin film transistor. An organic layer covers the first and second signal lines and the switching thin film transistor and the driving thin film transistor. A pixel electrode is disposed on the organic layer such that the pixel electrode is connected to the driving thin film transistor. A pixel defining layer is disposed on the organic layer, the pixel defining layer surrounding the pixel electrode. A light emitting member is disposed on the pixel electrode. The light emitting member comprises a compound represented by Formula 1, and a common electrode is disposed on the light emitting member.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
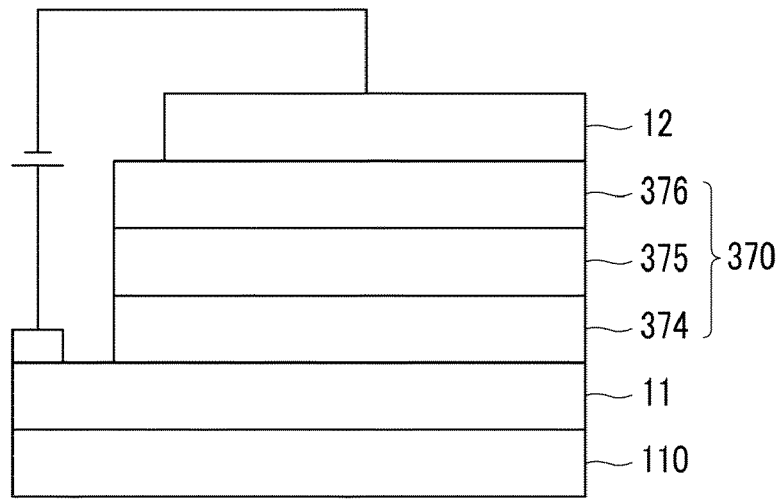
FIG. 1 is a schematic diagram of an organic light emitting device according to an exemplary embodiment of the present invention.

The invention is described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, portions may be omitted to clearly describe the present invention, and like reference numerals denote like elements.

Reference to "embodiment" or "an embodiment" means that a particular feature, structure, or characteristic described in connection with the embodiment is included in at least one embodiment of the invention. The appearances of the phrase "an embodiment" in various places in the specification are not necessarily all referring to the same embodiment, nor are separate or alternative embodiments mutually exclusive of other embodiments. Moreover, various features are described which may be exhibited by some embodiments and not by others. Detailed descriptions of well-known functions and structures incorporated herein may be omitted to avoid obscuring the subject matter of the present invention.

In the drawings, the size and relative size of layers, films, panels, regions, etc., may be exaggerated for clarity. It will be understood that when an element such as a layer, film, region, or substrate is referred to as being "on" another element, it can be directly on the other element or intervening elements may also be present. In contrast, when an element is referred to as being "directly on" another element, there are no intervening elements present. Likewise, it will be understood that when an element such as a layer, film, region, or substrate is referred to as being "under" another element, it can be directly under the other element or intervening elements may also be present. In contrast, when an element is referred to as being "directly under" another element, there are no intervening elements present.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

An organic compound according to an exemplary embodiment of the present invention is represented by Formula 1, and will now be described in detail.

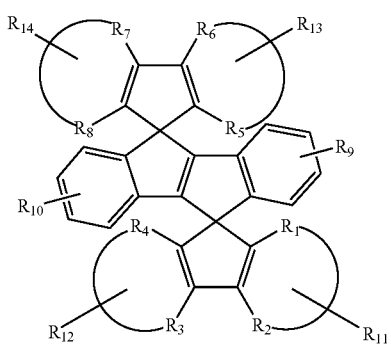

[Formula 1]

In Formula 1, each of $R_1$ and $R_2$, $R_3$ and $R_4$, $R_5$ and $R_6$, and $R_7$ and $R_8$ independently represents a 5 or 6-membered cyclic or linear substituent. $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may each represent hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —N($Z_1$)($Z_2$), or —Si($Z_3$)($Z_4$)($Z_5$), where each of $Z_1$ to $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

For example, $R_1$ and $R_2$ may form of a benzene ring, and in this case, $R_1$ may be a methyl group. $R_3$ and $R_4$ may each be a methyl group as a linear substituent, and in this case, $R_{12}$ is not formed. $R_5$ and $R_6$ may form of a pentagonal ring containing nitrogen, and $R_{13}$ may not be formed. $R_7$ and $R_8$ may each be a methyl group, and in this case, $R_{14}$ is not formed. Furthermore, $R_1$ and $R_2$ may form a benzene ring while $R_{11}$ may be a methyl group. $R_3$ and $R_4$, $R_5$ and $R_6$, and $R_7$ and $R_8$ may each form a benzene ring, and $R_{12}$, $R_{13}$ and $R_{14}$ may each be a methyl group. In addition, $R_1$ to $R_{14}$ may be substituents of various combinations.

Specifically, each of the alkyl group, alkoxy group, aryl group, heteroaryl group, cycloalkyl group and heterocycloalkyl group may have substituents of —F, —Cl, —Br, —CN, —NO₂, —OH, a non-substituted or (—F, —Cl, —Br, —CN, —NO₂, or —OH)-substituted C1-C40 alkyl group, a non-substituted or (—F, —Cl, —Br, —CN, —NO₂, or —OH)-substituted C1-C40 alkoxy group, a non-substituted or (C1-C40 alkyl group, C1-C40 alkoxy group, a —F, —Cl, —Br, —CN, —NO₂, or —OH)-substituted C6-C50 aryl group, a non-substituted or (C1-C40 alkyl, Cl -C40 alkoxy, —F, —Cl, —Br, —CN, —NO₂, or —OH)-substituted C2-C50 heteroaryl group, a non-substituted or (C1-C40 alkyl, C1-C40 alkoxy, —F, —Cl, —Br, —CN, —NO₂, or —OH)-substituted C5-C40 cycloalkyl group, a non-substituted or (C1-C40 alkyl, C1-C40 alkoxy radicals, —F, —Cl, —Br, —CN, —NO₂, or —OH)-substituted C5-C40 heterocycloalkyl group, or —N($Z_9$)($Z_{10}$). In this case, each of $Z_9$ and $Z_{10}$ may independently represent hydrogen, a C1-C40 alkyl group, or a (C1-C40 alkyl radicals)-substituted C6-C50 aryl group.

Specifically, each of $R_1$ to $R_{14}$ may represent hydrogen, a C1-C40 alkyl group, C1-C40 alkoxy group, phenyl group, biphenyl group, pentarenyl group, indenyl group, naphthyl group, biphenylrenyl group, anthracenyl group, azrenyl group, heptarenyl group, acenaphthylrenyl group, penarenyl group, fluorenyl group, methylantryl group, penantrenyl group, triphenylrenyl group, pirenyl group, chrysenyl group, ethyl-chrysenyl group, pisenyl group, perylrenyl group, chloropherylrenyl group, pentaphenyl group, pentasenyl group, tetraphenylrenyl group, hexaphenyl group, hexasenyl group, rubisenyl group, coronenyl group, trinaphthylrenyl group, heptaphenyl group, heptasenyl group, pirantrenyl group, obarenyl group, carbazollyl group, thiophenyl group, indollyl group, purinyl group, benzimidazolyl group, quinolinyl group, benzothiophenyl group, parathiazinyl group, pyrolyl group, pirazollyl group, imidazollyl group, imidazolinyl group, oxazollyl group, thiazollyl group, triazollyl group, tetrazolyl group, oxadiazollyl group, pyridinyl group, pyridazinyl group, pyrimidinyl group, pyrazinyl group, thianthrenyl group, cyclopentyl group, cyclohexyl group, oxiranyl group, pyrrolidinyl group, pyrazolidinyl group, imidazolidinyl group, piperidinyl group, piperazinyl group, morpholinyl group, di(C6-C30 aryl)amino group, or tri(C6-C30 aryl)silyl group.

As the compound represented by Formula 1 is well-dissolved in a solvent of toluene or chlorobenzene, it exerts the effect of improving the processing efficiency. Furthermore, as the compound represented by Formula 1 does not have a glass transition temperature Tg and has a very high boiling point, it has excellent thermal stability.

A method of manufacturing a compound according to an exemplary embodiment of the present invention will now be described in detail.

First, a compound represented by Formula 2 is prepared.

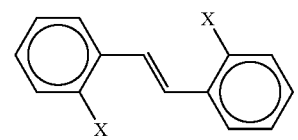

[Formula 2]

In Formula 2, X represents halogen elements of F, Br, Cl, and etc.

For example, the compound represented by Formula 2 may be generated by reacting stilbene through halogenation.

Then, a compound represented by Formula 3 is prepared.

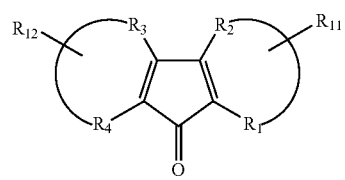

[Formula 3]

For example, a ketone group of the compound represented by Formula 3 may be generated through hydration and oxidation reactions. Furthermore, the substituent of $R_{11}$ or $R_{12}$ may be properly introduced by way of a Friedel-Crafts reaction.

Then, a first mixture is made by reacting the compound represented by Formula 2 with an organic metal compound in an organic solvent at a low temperature. At this time, the halogen elements of the compound represented by Formula 2 are substituted with metal ions. The organic solvent may be selected from tetrahydrofuran (THF) and dimethyl formamide (DMF). Examples of the organic metal compound may be lithium, nickel, and titanium compounds, which are substituted with C1-C10 alkyl, alkoxy, or C6-C30 aryl radicals. The reaction temperature may be about −50° C. or less, and the reaction time may be about 10 minutes to 1 hour.

Thereafter, the compound represented by Formula 3 is added to the first mixture. The first mixture including the compound represented by Formula 3 is heated to room temperature and allowed to react for 12 hours to 36 hours to thereby form a second mixture. At this time, the metal ion-substituted compound represented by Formula 2 reacts with the compound represented by Formula 3 to thereby generate a compound represented by Formula 4.

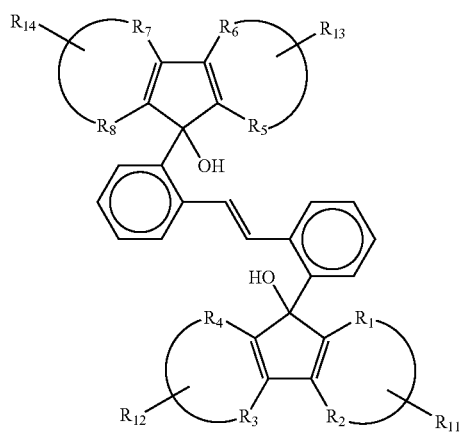

[Formula 4]

When the second mixture reacts under an acid catalyst, a compound represented by Formula 1 is generated. The acid catalyst may be selected from hydrochloric acid, sulfuric acid, and acetic acid.

Thereafter, filtering, cleaning, drying, and purifying are conducted so as to obtain the compound represented by Formula 1.

A method of manufacturing a compound according to an exemplary embodiment of the present invention will now be described in detail.

First, a compound represented by Formula 5 is prepared.

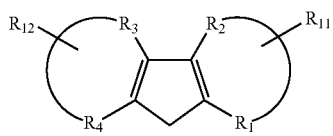

[Formula 5]

For example, the substituents of $R_{11}$ or $R_{12}$ may be properly introduced by the Friedel-Crafts reaction.

Thereafter, the compound represented by Formula 5 reacts with benzaldehyde under a base catalyst, and undergoes a halogenation reaction to thereby form a third mixture. At this time, a compound represented by Formula 6 is generated through the halogenation reaction. The base catalyst may be selected from potassium hydroxide and sodium hydroxide.

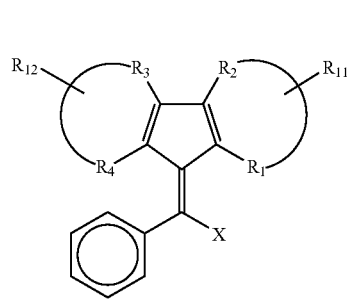

[Formula 6]

Then, the third mixture reacts with an organic metal compound in an organic solvent to thereby form a fourth mixture. At this time, the halogen elements of the compound represented by Formula 6 are substituted with metal ions so that a compound represented by Formula 7 is generated. The organic solvent may be selected from tetrahydrofuran (THF) and dimethyl formamide (DMF). The organic metal compound may be selected from metal compounds of lithium, nickel, and titanium, which are substituted with C1-C10 alkyl, alkoxy, or C6-C30 aryl radicals.

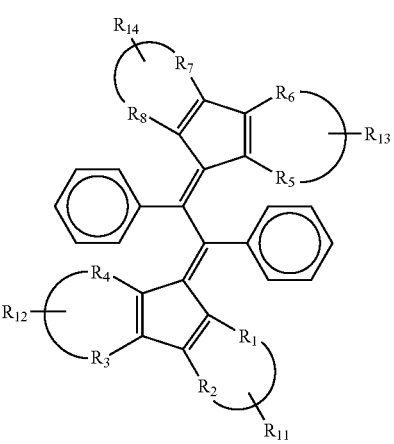

[Formula 7]

When the fourth mixture reacts under an acid catalyst, a compound represented by Formula 1 is generated. The acid catalyst may be selected from hydrochloric acid, sulfuric acid, and acetic acid.

Then, filtering, cleaning, drying, and purifying are conducted to thereby obtain a compound represented by Formula 1.

An organic light emitting device according to an exemplary embodiment of the present invention will now be described in detail with reference to FIG. 1.

FIG. 1 is a schematic diagram of an organic light emitting device according to an exemplary embodiment of the present invention.

An anode 11 is formed on a substrate 110. The anode 11 may be formed with a material having a sufficient work function so as to cause the injection of holes, for example, with a transparent oxide selected from indium tin oxide (ITO) and other indium oxides.

An organic light emitting member 370 is formed on the anode 11. The organic light emitting member 370 includes a hole transport layer (HTL) 374, an emission layer (EL) 375, and an electron transport layer (ETL) 376.

The hole transport layer 374 and the electron transport layer 376 balance the electrons and holes with each other, and the emission layer 375 emits light of any one of three primary colors of red, green, and blue.

The emission layer 375 contains a host material and a dopant material. The host material contains a compound represented by Formula 1. The dopant material may also contain a compound represented by Formula 1.

The hole transport layer 374 may contain a p-type semiconductor, and the electron transport layer 376 may contain an organic metal complex compound, an organic ion compound, a metal ion compound, an n-type semiconductor, or mixtures thereof. The hole transport layer 374 and the electron transport layer 376 may contain a compound represented by Formula 1.

The organic layers of the hole transport layer 374, the emission layer 375, and the electron transport layer 376 may be formed through vacuum deposition or solution spraying, depending upon the device and fabrication method. In an embodiment where the solution spraying such as inkjet printing, screen printing, and spin coating is used, the processing steps are simplified with low production cost, and hence excellent resolution can be obtained compared to the case of using a shadow mask. In order for the organic layers to contain various compounds, a co-deposition technique may be introduced.

A cathode 12 is formed on the electron transport layer 376. The cathode 12 may be formed with a material having a low work function so as to make it easy to inject electrons into the electron transport layer 376. For example, the cathode 12 may be formed with metals such as magnesium, calcium, sodium, potassium, titanium, indium, yttrium, lithium, gadolinium, aluminum, gold, silver, platinum, nickel, copper, tungsten, tin, lead, cesium, barium, and alloys thereof, or multi-layered structure materials such as LiF/Al, $LiO_2$/Al, LiF/Ca, and $BaF_2$/Ca.

An organic light emitting device according to another exemplary embodiment of the present invention will now be described in detail with reference to FIG. 2.

Figure 2:
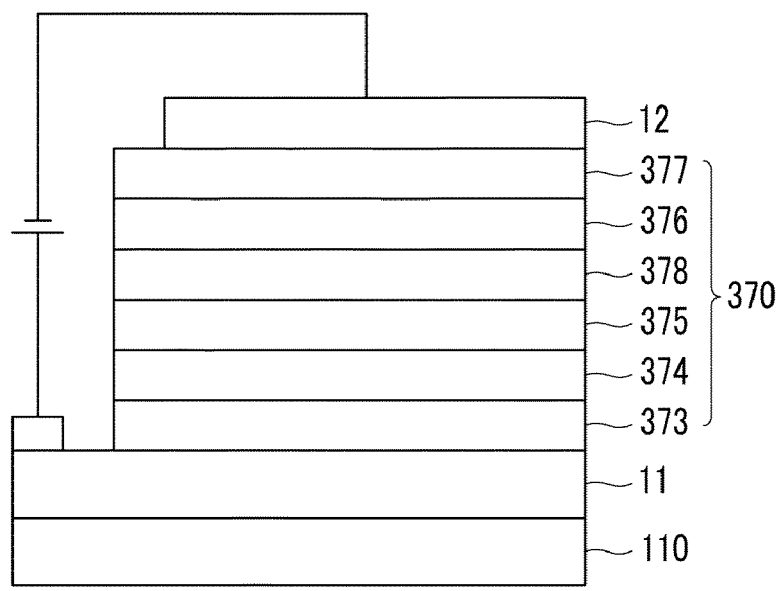
FIG. 2 is a schematic diagram of an organic light emitting device according to another exemplary embodiment of the present invention.

FIG. 2 is a schematic diagram of an organic light emitting device according to another exemplary embodiment of the present invention. The organic light emitting device shown in FIG. 2 is the same in structure as that shown in FIG. 1 except that a hole injecting layer 373 is interposed between the anode 11 and the hole transport layer 374, an electron injecting layer 377 is interposed between the cathode 12 and the electron transport layer 376, and a hole blocking layer 378 is interposed between the emission layer 375 and the electron transport layer 376. The hole injecting layer 373 and the electron injecting layer 377 serve to reinforce the injection of holes and electrons, respectively. The hole injecting layer 373, the electron injecting layer 377, and the hole blocking layer 378 may contain a compound represented by Formula 1. In an optional embodiment, the hole blocking layer 378 may be omitted.

Figure 3:
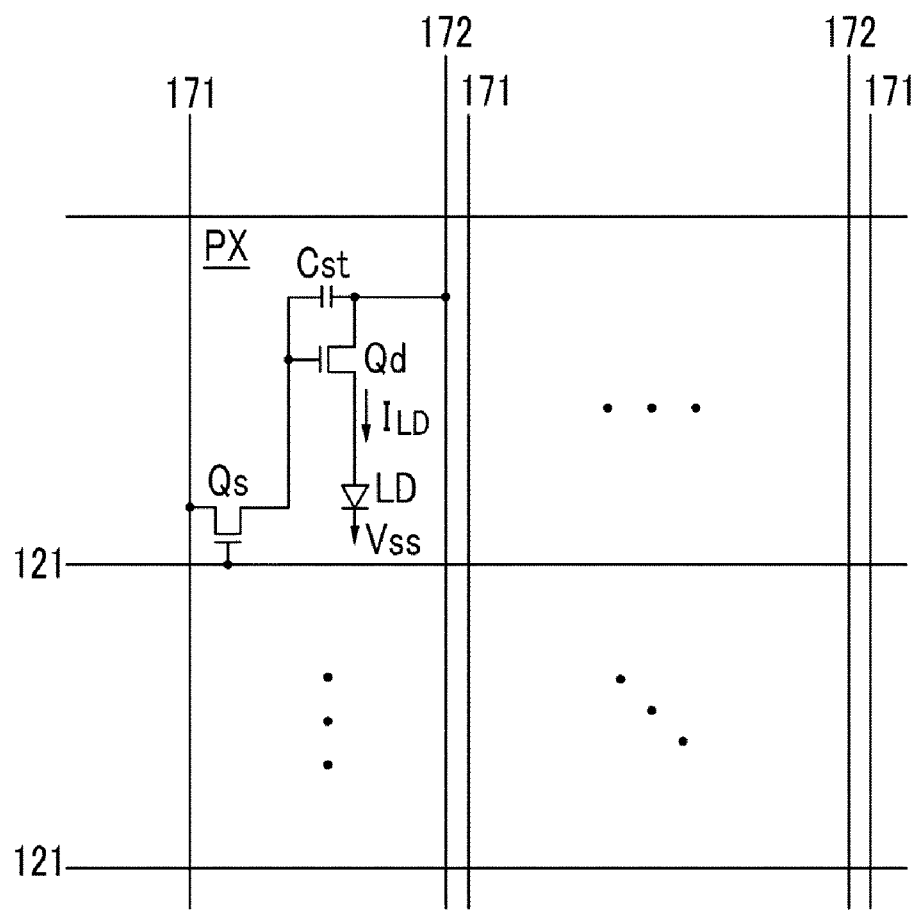
FIG. 3 is an equivalent circuit diagram of an organic light emitting display according to an exemplary embodiment of the present invention.

An organic light emitting display according to yet another exemplary embodiment of the present invention will now be described in detail with reference to FIG. 3. FIG. 3 is an equivalent circuit diagram of an organic light emitting display according to an exemplary embodiment of the present invention. Referring to FIG. 3, the organic light emitting display according to the present exemplary embodiment includes a plurality of signal lines 121, 171, and 172, and a plurality of pixels PX connected thereto while arranged roughly in the form of a matrix.

The signal lines include a plurality of gate lines 121 for transmitting gate signals (or scanning signals), a plurality of data lines 171 for transmitting data signals, and a plurality of driving voltage lines 172 for transmitting driving voltages. The gate lines 121 proceed roughly in the row direction while being arranged substantially parallel to each other, and the data lines 171 and the driving voltage lines 172 proceed roughly in the column direction while being arranged substantially parallel to each other.

The pixels PX each have a switching thin film transistor Qs, a driving thin film transistor Qd, a storage capacitor Cst, and an organic light emitting diode (OLED) LD.

The switching thin film transistor Qs has a control terminal, an input terminal, and an output terminal. The control terminal of the switching thin film transistor Qs is connected to the gate line 121, the input terminal thereof is connected to the data line 171, and the output terminal thereof is connected to the driving thin film transistor Qd. The switching thin film transistor Qs transmits a data signal applied to the data line 171 to the driving thin film transistor Qd, in response to the scanning signal applied to the gate line 121.

The driving thin film transistor Qd also has a control terminal, an input terminal, and an output terminal. The control terminal of the driving thin film transistor Qd is connected to the switching thin film transistor Qs, the input terminal thereof is connected to the driving voltage line 172, and the output terminal thereof is connected to the organic light emitting diode LD. The driving thin film transistor Qd makes the flow of output currents ILD differentiated in dimension depending upon the voltages between its control and output terminals.

The storage capacitor Cst is disposed between the control and input terminals of the driving thin film transistor Qd such that it interconnects those terminals. The storage capacitor Cst is charged with the data signals applied to the control terminal of the driving thin film transistor Qd, and stores them even after the switching thin film transistor Qs turns off.

The organic light emitting diode LD, which includes an organic light emitting device according to an exemplary embodiment of the present invention, has an anode connected to the output terminal of the driving thin film transistor Qd and a cathode connected to a common voltage Vss. The organic light emitting diode LD emits light that is differentiated in intensity depending upon the output currents ILD of the driving thin film transistor Qd to thereby display images.

The switching thin film transistor Qs and the driving thin film transistor Qd each are an n-channel field effect transistor (FET). However, at least one of the switching thin film transistor Qs and the driving thin film transistor Qd may be a p-channel field effect transistor. Furthermore, the interconnection relationships among the thin film transistors Qs and Qd, the storage capacitor Cst, and the organic light emitting diode LD may be changed.

The specific structure of the organic light emitting display shown in FIG. 3 will now be described with reference to FIG. 4 and FIG. 5 as well as FIG. 3.

Figure 4:
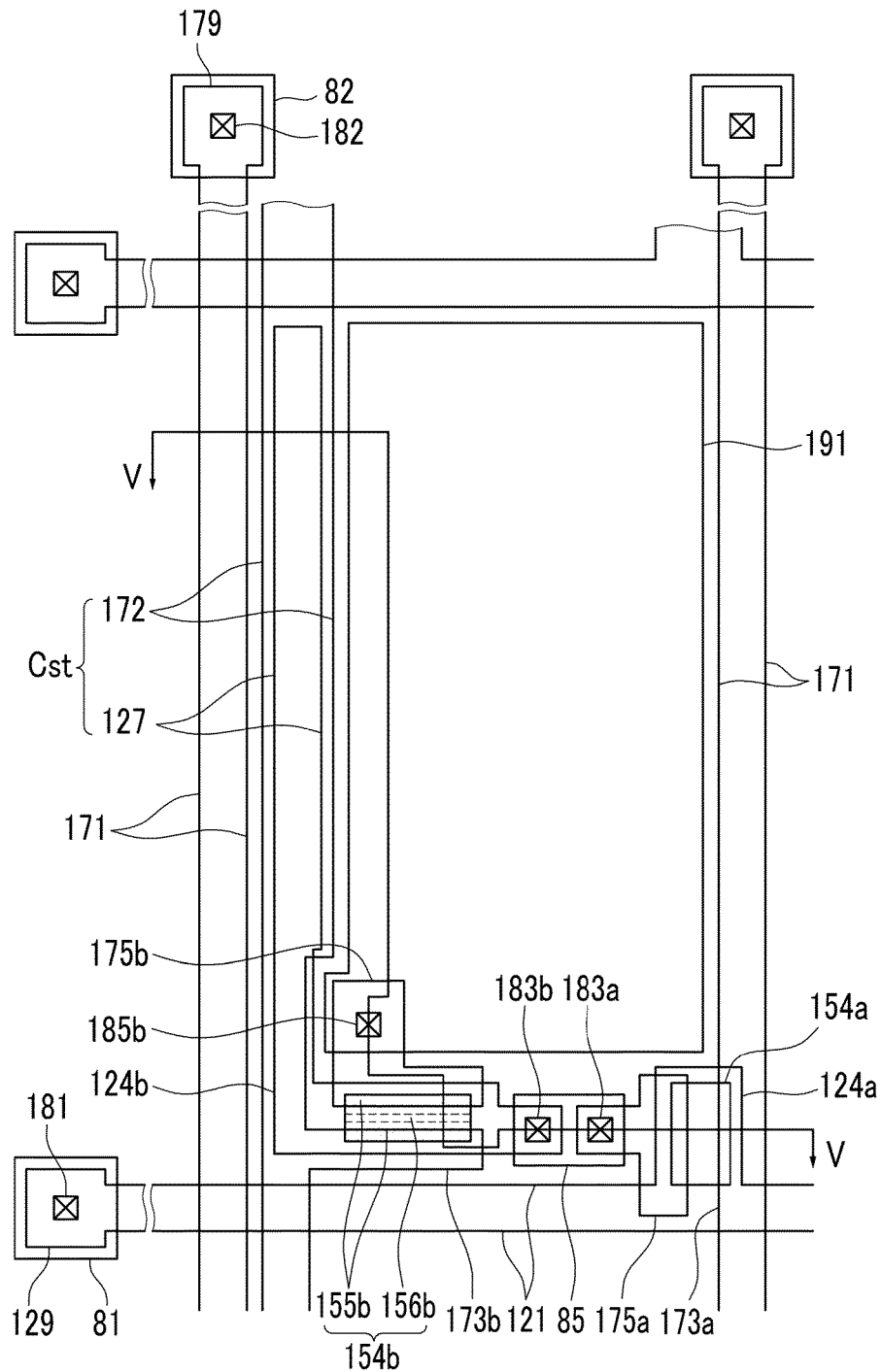
FIG. 4 is a layout view of an organic light emitting display according to an exemplary embodiment of the present invention.
Figure 5:
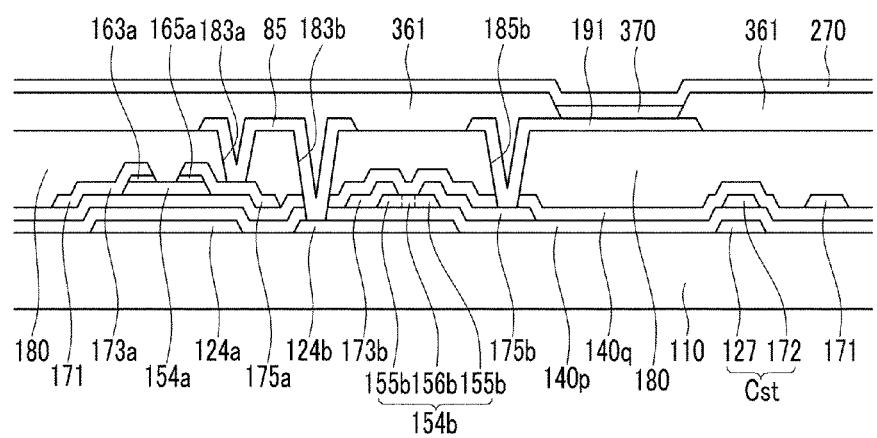
FIG. 5 is a cross-sectional view taken along the V-V line of FIG. 4.

FIG. 4 is a layout view of an organic light emitting display according to an exemplary embodiment of the present invention, and FIG. 5 is a cross-sectional view of the organic light emitting display shown in FIG. 4 taken along the V-V line thereof.

An insulation substrate 110 comprising transparent glass or plastic is prepared. The insulation substrate 110 may be previously heat-treated through pre-compaction. The pre-compaction is to previously heat-treat the substrate at about 500 to 800° C. such that it is thermally expanded and contracted.

Gate lines 121 with switching control electrodes 124a, and driving control electrodes 124b are formed on the insulation substrate 110.

Each of the gate lines 121, which extend along a horizontal direction of the substrate, has a switching control electrode 124a extended upward, and an end portion 129 to be connected with an external driving circuit.

The driving control electrode 124b is separated from the gate line 121, and has a storage electrode 127 elongated upward.

The gate line 121 and the driving control electrode 124b may be formed with a refractory metal such as a molybdenum-containing metal with the content of molybdenum (Mo) or a molybdenum alloy, a chromium-containing metal with the content of chromium (Cr) or a chromium alloy, a titanium-containing metal with the content of titanium (Ti) or a titanium alloy, a tantalum-containing metal with the content of tantalum (Ta) or a tantalum alloy, and a tungsten-containing metal with the content of tungsten (W) or a tungsten alloy, or a low resistance metal such as aluminum (Al), copper (Cu), and silver (Ag).

A driving gate insulating layer 140p is formed on the gate line 121 and the driving control electrode 124b. The driving gate insulating layer 140p may be formed with silicon nitride (SiNx) or silicon oxide (SiO$_2$), and may have a thickness of about 500 Å to about 2000 Å.

A driving semiconductor 154b is formed on the driving gate insulating layer 140p such that it is overlapped with the driving control electrode 124b. The driving semiconductor 154b is island-shaped, and may be formed with crystalline silicon such as microcrystalline silicon and polycrystalline silicon.

The driving semiconductor 154b contains doped regions 155b and non-doped regions 156b. The doped regions 155b are located at both sides of the non-doped regions 156b while having the latter in the center thereof. The doped regions 155b are formed with crystalline silicon doped with p-type impurities such as boron (B) or n-type impurities such as phosphorus (P). The non-doped region 156b is formed with a non-doped intrinsic semiconductor, and forms a channel for the driving thin film transistor.

A driving voltage line 172 with a driving input electrode 173b and a driving output electrode 175b are formed on the driving semiconductor 154b and the driving gate insulating layer 140p.

The driving voltage lines 172 proceed roughly in the vertical direction such that they cross the gate lines 121, and transmit driving voltages. The driving voltage line 172 has the driving input electrode 173b extended over the driving semiconductor 154b, and is partially overlapped with the storage electrode 127 of the driving control electrode 124b so as to form a storage capacitor Cst.

The driving output electrode 175b is spaced apart from the driving voltage line 172, and is island-shaped.

The driving input electrode 173b and the driving output electrode 175b are placed on respective doped regions 155b of the driving semiconductor 154b to face each other across the non-doped region 156b of the driving semiconductor 154b. The driving input electrode 173b is spaced apart from the non-doped region 156b by the same distance as the driving output electrode 175b is spaced apart from the non-doped region 156b. The space between the driving input electrode 173b and the non-doped region 156b and the space between the driving output electrode 175b and the non-doped region 156b is referred to as an offset.

The driving voltage line 172 and the driving output electrode 175b may be formed with the previously-mentioned refractory metal or low resistance metal such as aluminum (Al), copper (Cu), and silver (Ag), and may have a multi-layered structure of molybdenum (Mo)/aluminum (Al)/molybdenum (Mo) as well as a single-layered structure. With the case of the multi-layered structure, the layers of molybdenum (Mo)/aluminum (Al)/molybdenum (Mo) may have a thickness of about 300 Å, about 2500 Å, and about 1000 Å, respectively.

A switching gate insulating layer 140q is formed on the driving voltage line 172 and the driving output electrode 175b. The switching gate insulating layer 140q may be formed with silicon nitride (SiNx), and may have a thickness in a range from about 3000 Å to about 4500 Å.

A switching semiconductor 154a is formed on the switching gate insulating layer 140q such that it is overlapped with the switching control electrode 124a. The switching semiconductor 154a may be formed with amorphous silicon, and may have a thickness in a range from about 1500 Å to about 2500 Å.

A pair of ohmic contacts 163a and 165a are formed on the switching semiconductor 154a. The ohmic contacts 163a and 165a may be formed with amorphous silicon doped with n-type or p-type impurities, and have a thickness of about 500 Å.

A data line 171 with a switching input electrode 173a, and a switching output electrode 175a, are formed on the ohmic contacts 163a and 165a and the switching gate insulating layer 140q.

The data lines 171 proceed roughly in the vertical direction such that they cross the gate lines 121, and transmit data signals. Each data line 171 is partially overlapped with the switching semiconductor 154a so as to form a switching input electrode 173a.

A switching output electrode 175a faces the switching input electrode 173a on the switching semiconductor 154a.

The data line 171 and the switching output electrode 175a may be formed with the previously-described refractory metal or low resistance metal such as aluminum (Al), copper (Cu), and silver (Ag), and may have a multi-layered structure of molybdenum (Mo)/aluminum (Al)/molybdenum (Mo) as well as a single-layered structure. With the case of the multi-layered structure, the layers of molybdenum (Mo)/aluminum (Al)/molybdenum (Mo) may have a thickness of about 300 Å, about 2500 Å, and about 1000 Å, respectively.

A passivation layer 180 is formed on the data line 171 and the switching output electrode 175a. The passivation layer 180 may be formed with an organic material having an excellent flattening characteristic such as a polyacryl, and have a thickness in a range from about 2000 Å to 2 μm.

Contact holes 183a and 182 are formed in the passivation layer 180 to expose the switching output electrode 175a and the end portion 179 of the data line 171, respectively, and another contact hole 185b is formed in the passivation layer 180 and switching gate insulating layer 140q to expose the driving output electrode 175b. Still other contact holes 183b and 181 are formed in the passivation layer 180, the switching gate insulating layer 140q, and the driving gate insulating layer 140p to expose the driving control electrode 124b and the end portion 129 of the gate line 121, respectively.

A pixel electrode 191, a connector 85, and contact assistants 81 and 82 are formed on the passivation layer 180.

The pixel electrode 191 is electrically connected to the driving output electrode 175b through the contact hole 185b. The pixel electrode 191 may be formed with a transparent conductor such as indium tin oxide (ITO) or indium zinc oxide (IZO).

The connector 85 electrically interconnects the switching output electrode 175a and the driving control electrode 124b through the contact holes 183a and 183b.

The contact assistants 81 and 82 are connected to the end portion 129 of the gate line 121 and the end portion 179 of the data line 171 through the contact holes 181 and 182, respectively. The contact assistants 81 and 82 serve to assist the adhesion of the end portion 129 of the gate line 121 and the end portion 179 of the data line 171, respectively, to external units, and to protect them.

A pixel defining layer 361 is formed on the passivation layer 180 and the connector 85. The pixel defining layer 361 surrounds the periphery of the pixel electrode 191 like a bank. The pixel defining layer 361 may be formed with an organic insulating material.

A light emitting member 370 is formed on the pixel electrode 191. The light emitting member 370 may appropriately include the structural components of an organic light emitting device according to an exemplary embodiment of the present invention, such as a hole injecting layer 373, a hole transport layer 374, an emission layer 375, a hole blocking layer 378, an electron transport layer 376, and an electron injecting layer 377. In addition, at least one of the emission layer, the electron transport layer, the electron injecting layer, the hole transport layer, the hole injecting layer, and the hole blocking layer may contain a compound represented by Formula 1.

A common electrode 270 is formed on the light emitting member 370. The common electrode 270 may be formed on the entire surface of the substrate with an opaque conductor, such as gold (Au), platinum (Pt), nickel (Ni), copper (Cu), tungsten (W), and alloys thereof.

The common electrode 270 and the pixel electrode 191 as a pair cause the flow of electrical current to the light emitting member 370. The pixel electrode 191, the organic light emitting member 370, and the common electrode 270 form a light emitting diode (LED) LD. In this embodiment, the pixel electrode 191 may function as an anode and the common electrode 270 may function as a cathode, or to the contrary in an optional embodiment, the pixel electrode 191 may function as the cathode and the common electrode 270 may function as the anode.

Meanwhile, the inter-layered structure and disposition of the switching thin film transistor and the driving thin film transistor may be altered in various manners, in addition to as above-identified.

The present invention will now be described further in detail by way of examples, but is not limited thereto.

EXAMPLE 1

Preparation of Organic Compound

Fluorene and 2,6-di-t-butyl-p-cresol were added to nitromethane and AlCl$_3$ as a catalyst, and allowed to react at 10-15° C. for 1 hour, thereby preparing a compound represented by Formula 8.

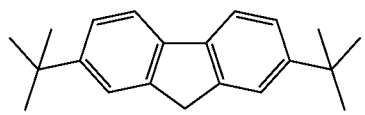

[Formula 8]

The compound represented by Formula 8 and benzyltrimethyl ammonium hydroxide were added to pyridine, and allowed to react at room temperature for 5 hours, thereby preparing a compound represented by Formula 9.

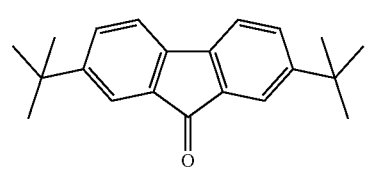

[Formula 9]

Meanwhile, benzaldehyde was halogenated under bromine gas to thereby prepare benzaldehyde bromide. The benzaldehyde bromide, TiCl$_4$, and zinc were added to THF to thereby prepare a compound represented by Formula 10.

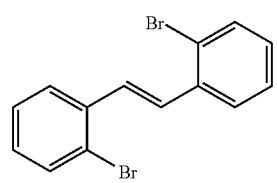

[Formula 10]

Thereafter, the compound represented by Formula 10 and t-butyllithium were added to THF, and allowed to react at about −78° C. for about 30 minutes. The compound represented by Formula 9 was added to the mixture, and after heating it to room temperature, it was allowed to react at room temperature for about 24 hours, thereby preparing a compound represented by Formula 11.

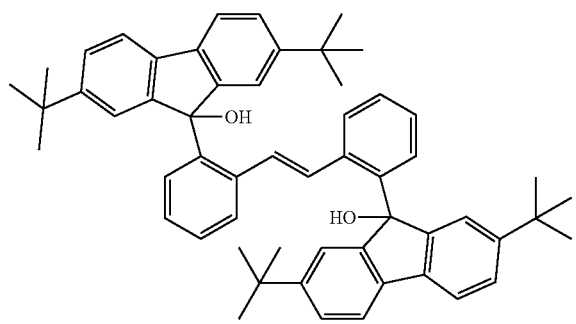

[Formula 11]

Then, hydrochloric acid and acetic acid were added to the compound represented by Formula 11 and allowed to react, thereby preparing a compound represented by Formula 12.

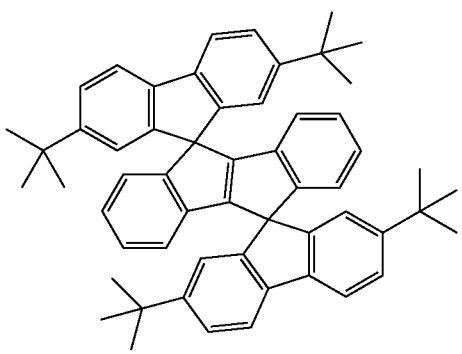

[Formula 12]

Fabrication of Organic Light Emitting Device

A glass substrate based on 15 Ω/cm² (1000 Å) ITO was cut to a size of 50 mm×50 mm×0.7 mm, and was ultrasonic wave cleaned in acetone isopropyl alcohol and then in purified water for 15 minutes, respectively, followed by UV ozone-cleaning for 30 minutes to form an anode. A compound of 4,4',4''-tris(N,N-diphenylamino)triphenylamine (mTDATA) was vacuum-deposited onto the ITO glass substrate to form a hole injecting layer with a thickness of 600 Å, and a compound of N,N'-di(naphthalene-1-yl)-N,N'-diphenyl-benzidine (NPB) was vacuum-deposited onto the hole injecting layer to form a hole transport layer with a thickness of 300 Å. A compound represented by Formula 12 as a host and a compound of 4,4'-bis[2-{4-(N,N-diphenylamino) phenyl}vinyl]biphenyl (DPAVBi) as a dopant were vacuum deposited onto the hole transport layer in a weight ratio of 100:5 to form an emission layer with a thickness of 300 Å. Thereafter, Alq3 (aluminum trisquinolinolate) was deposited onto the emission layer to thereby form an electron transport layer with a thickness of 250 Å. LiF was vacuum-deposited onto the electron transport layer to form an electron injecting layer with a thickness of 6 Å, and Al was vacuum-deposited onto the electron injecting layer to form a cathode with a thickness of 1500 Å. In this way, an organic light emitting device was fabricated.

EXAMPLE 2

Preparation of Organic Compound

Fluorene and benzaldehyde were reacted with each other under potassium hydroxide to form a mixture. Thereafter, acetic acid was added to the mixture under an atmosphere of bromine gas and heated, to thereby form a compound represented by Formula 13.

[Formula 13]

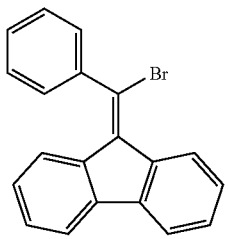

Bipyridyl, cyclooctadiene nickel, and the compound represented by Formula 13 were added to DMF and allowed to react, thereby preparing a compound represented by Formula 14.

[Formula 14]

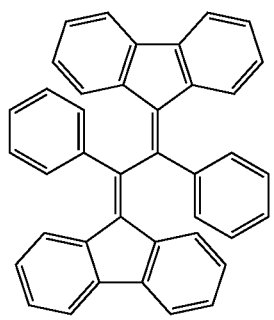

Sulfuric acid was added to the compound represented by Formula 14 and allowed to react, thereby preparing a compound represented by Formula 15.

[Formula 15]

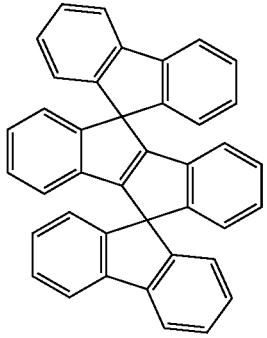

Fabrication of Organic Light Emitting Device

An organic light emitting device was fabricated through the same processing steps as those related to Example 1, except that the compound represented by Formula 15 was used as a host material for the emission layer instead of the compound represented by Formula 12.

COMPARATIVE EXAMPLE 1

An organic light emitting device was fabricated through the same processing steps as those related to Example 1, except that a compound of 2-t-butyl-9,10-di-(2-naphthyl)anthracene (TBADN) was used as a host material for the emission layer instead of the compound represented by Formula 12.

Figure 6:
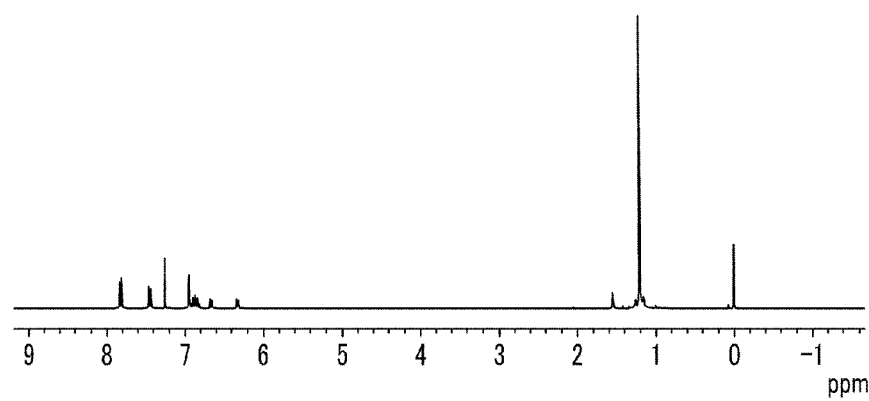
FIG. 6 is a 1H NMR graph of an organic compound according to an exemplary embodiment of the present invention.

FIG. 6 illustrates the 1H NMR measurements of the compound represented by Formula 12 that was fabricated according to Example 1, and the data are as follows.

1H NMR (300 MHz, CDCl3) 7.82 (d, J=8.1 Hz, 4H), 7.45 (dd, J=6.3, 1.8 Hz, 4H), 6.95 (s, 4H), 6.88 (m, 4H), 6.67 (d, J=6.9 Hz, 2H), 6.33 (d, J=7.5 Hz, 2H), 1.21 (s, 36H); MS (ES-TOF) m/z 751.42 (M+Na)+.

The data indicate peak values corresponding to the respective atomic bonds in the 1H NMR graph, and it can be known from the data that a compound represented by Formula 12 was fabricated.

Figure 7:
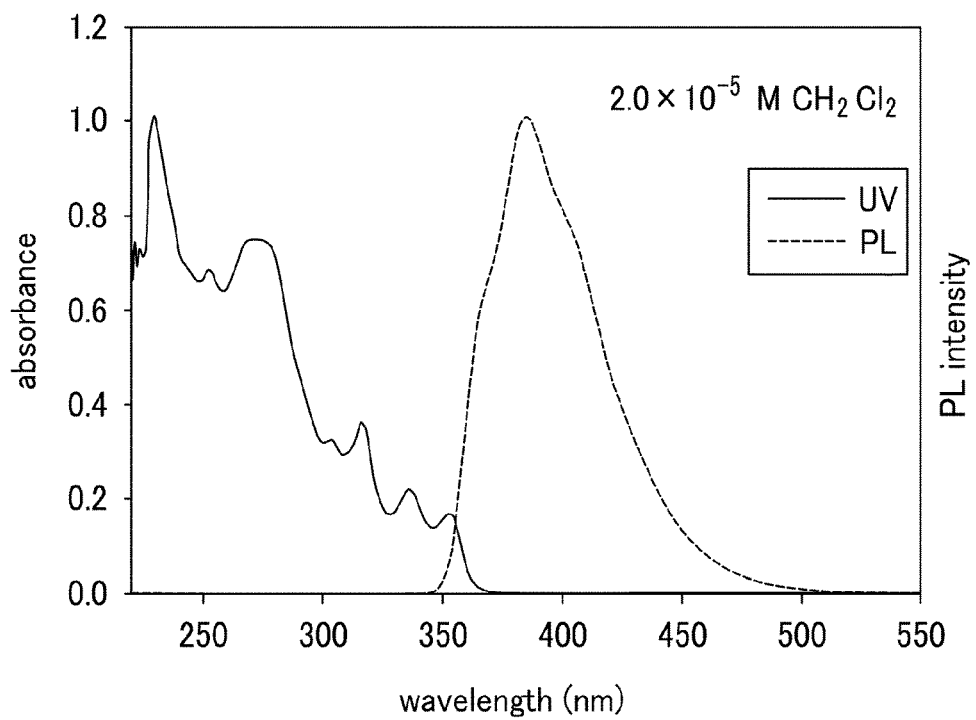
FIG. 7 is an absorption spectrum and emission spectrum graph of an organic compound according to an exemplary embodiment of the present invention.

FIG. 7 illustrates the measurements of the absorption and emission spectrums of the compound represented by Formula 12 that was fabricated according to Example 1.

As shown in FIG. 7, the peaks in absorption wavelengths occurred at 232 nm, 275 nm, 318 nm, and 335 nm, respectively. With the emission wavelengths, the excited state occurred at 350 nm, and the peak occurred at 385 nm. The photon efficiency was very high at 87%, which was measured based on 90% of the photon efficiency of 9,10-diphenylanthracene in cyclohexane. The energy levels of HOMO (that is, the energy level of the highest occupied molecular orbital) and LUMO (the energy level of the lowest unoccupied molecular orbital) were −5.04 eV and −1.16 eV, respectively. The band gap was large at 3.88 eV.

The compound represented by Formula 12, which was prepared according to the Example 1, did not have a glass transition temperature, and had a boiling point of 397° C. Compared to the case of TBAIN according to Comparative Example 1 where the glass transition temperature was 129° C.

and the boiling point was 291° C., it can be known that the compound represented by Formula 12 has excellent thermal stability.

The driving voltage, the current efficiency, and the color coordinate of the organic light emitting devices fabricated according to Example 1, Example 2 and the Comparative Example 1 were measured, and the measurement results are listed in Table 1.

TABLE 1

| | Driving voltage | Current efficiency (cd/A) | Color coordinate |
|---|---|---|---|
| Example 1 | 3.5 | 7.40 | (0.14, 0.25) |
| Example 2 | 3.6 | 7.36 | (0.14, 0.26) |
| Comparative Example 1 | 5.2 | 7.22 | (0.16, 0.29) |

Compared to Comparative Example 1, Example 1 and Example 2 had low driving voltage, and high current efficiency which is related to emission efficiency. Furthermore, as the blue color exhibits a coordinate of (0.14, 0.08) based on NTSC (National Television System Committee), wherein the NTSC is an organization that formulates standards for the current U.S. color television system and most countries of the Americas, the color coordinates related to Example 1 and Example 2 are closer to the blue color when compared with that related to the Comparative Example 1, so it can be known that the color purity thereof is high.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their.

What is claimed is:

1. A compound represented by Formula 1:

[Formula 1]

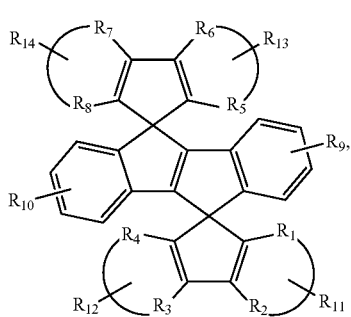

wherein each of $R_1$ and $R_2$, $R_3$ and $R_4$, $R_5$ and $R_6$, and $R_7$ and $R_8$ independently represents a 5 or 6-membered cyclic and $R_9$, $R_{10}$, $R_{11}$, $R_{12}$, $R_{13}$, and $R_{14}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, $-N(Z_1)(Z_2)$, or $-Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group, or wherein each of $R_1$, $R_2$, $R_3$, $R_4$, $R_5$, $R_6$, $R_7$, and $R_8$ represents hydrogen, a substituted or non-substituted C1-C50 alkyl group, a substituted or non-substituted C1-C50 alkoxy group, a substituted or non-substituted C6-50 aryl group, a substituted or non-substituted C2-C50 heteroaryl group, a substituted or non-substituted C5-C50 cycloalkyl group, a substituted or non-substituted C5-C30 heterocycloalkyl group, $-N(Z_1)(Z_2)$, or $-Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

2. The compound of claim 1, wherein each of the alkyl group, alkoxy group, aryl group, heteroaryl group, cycloalkyl group and heterocycloalkyl group has substituents of $-F$, $-Cl$, $-Br$, $-CN$, $-NO_2$, $-OH$, a non-substituted or ($-F$, $-Cl$, $-Br$, $-CN$, $-NO_2$, or $-OH$)-substituted C1-C40 alkyl group, a non-substituted or ($-F$, $-Cl$, $-Br$, $-CN$, $-NO_2$, or $-OH$)-substituted C1-C40 alkoxy group, a non-substituted or (C1-C40 alkyl group, C1-C40 alkoxy group, a $-F$, $-Cl$, $-Br$, $-CN$, $-NO_2$, or $-OH$)-substituted C6-C50 aryl group, a non-substituted or (C1-C40 alkyl, C1-C40 alkoxy, $-F$, $-Cl$, $-Br$, $-CN$, $-NO_2$, or $-OH$)-substituted C2-C50 heteroaryl group, a non-substituted or (C1-C40 alkyl, C1-C40 alkoxy, $-F$, $-Cl$, $-Br$, $-CN$, $-NO_2$, or $-OH$)-substituted C5-C40 cycloalkyl group, a non-substituted or (C1-C40 alkyl, C1-C40 alkoxy radicals, $-F$, $-Cl$, $-Br$, $-CN$, $-NO_2$, or $-OH$)-substituted C5-C40 heterocycloalkyl group, or $-N(Z_9)(Z_{10})$, where each of $Z_9$ and $Z_{10}$ independently represents hydrogen, a C1-C40 alkyl group, or a (C1-C40 alkyl radicals)-substituted C6-C50 aryl group.

3. The compound of claim 2, wherein each of $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ represents hydrogen, a C1-C40 alkyl group, C1-C40 alkoxy group, phenyl group, biphenyl group, pentarenyl group, indenyl group, naphthyl group, biphenylrenyl group, anthracenyl group, azrenyl group, heptarenyl group, acenaphthylrenyl group, penarenyl group, fluorenyl group, methylantryl group, penantrenyl group, triphenylrenyl group, pirenyl group, chrysenyl group, ethyl-chrysenyl group, pisenyl group, perylrenyl group, chloropherylrenyl group, pentaphenyl group, pentasenyl group, tetraphenylrenyl group, hexaphenyl group, hexasenyl group, rubisenyl group, coronenyl group, trinaphthylrenyl group, heptaphenyl group, heptasenyl group, pirantrenyl group, obarenyl group, carbazollyl group, thiophenyl group, indollyl group, purinyl group, benzimidazolyl group, quinolinyl group, benzothiophenyl group, parathiazinyl group, pyrolyl group, pirazollyl group, imidazollyl group, imidazolinyl group, oxazollyl group, thiazollyl group, triazollyl group, tetrazolyl group, oxadiazollyl group, pyridinyl group, pyridazinyl group, pyrimidinyl group, pyrazinyl group, thianthrenyl group, cyclopentyl group, cyclohexyl group, oxiranyl group, pyrrolidinyl group, pyrazolidinyl group, imidazolidinyl group, piperidinyl group, piperazinyl group, morpholinyl group, di(C6-C30 aryl)amino group, or tri(C6-C30 aryl)silyl group.

4. A method of manufacturing a compound, comprising:
reacting a compound represented by Formula 2 with an organic metal compound in an organic solvent to form a first mixture;

mixing a compound represented by Formula 3 with the first mixture to form a second mixture; and reacting the second mixture under an acid catalyst to form a compound represented by Formula 1:

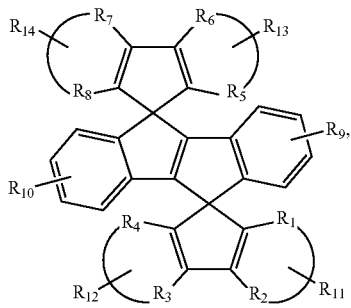

[Formula 1]

wherein each of $R_1$ and $R_2$, $R_3$ and $R_4$, $R_5$ and $R_6$, and $R_7$ and $R_8$ independently represents a 5 or 6-membered cyclic and $R_9$, $R_{10}$, $R_{11}$, $R_{12}$, $R_{13}$, and $R_{14}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —N($Z_1$)($Z_2$), or —Si($Z_3$)($Z_4$)($Z_5$), where each of $Z_1$, $Z_2$, $Z_3$, $Z_4$, and $Z_5$ independently represents hydrogen a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group, or wherein each of $R_1$, $R_2$, $R_3$, $R_4$, $R_5$, $R_6$, $R_7$, and $R_8$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —N($Z_1$)($Z_2$), or —Si($Z_3$)($Z_4$)($Z_5$), where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group,

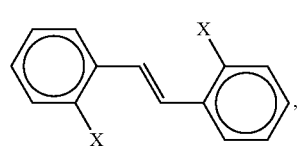

[Formula 2]

wherein X represents F, Br or Cl,

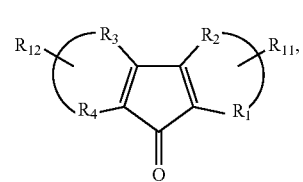

[Formula 3]

wherein each of $R_1$ and $R_2$, and $R_3$ and $R_4$ independently represents a 5 or 6-membered cyclic and $R_{11}$, and $R_{12}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —N($Z_1$)($Z_2$), or —Si($Z_3$)($Z_4$)($Z_5$), where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group, or wherein each of $R_1$, $R_2$, $R_3$, and $R_4$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —N($Z_1$)($Z_2$), or —Si($Z_3$)($Z_4$)($Z_5$), where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

5. The method of claim 4, wherein, in the forming of the first mixture, the reaction occurs at about −50° C. or less for about 10 minutes to 1 hour.

6. The method of claim 5, wherein, in the forming of the second mixture, after heating the first mixture including the compound represented by Formula 3 to room temperature, reacting the first mixture including the compound represented by Formula 3 at room temperature for about 12 to 36 hours to form the second mixture.

7. The method of claim 4, further comprising preparing the compound represented by Formula 2 by reacting a stilbene-based compound through halogenation.

8. The method of claim 4, further comprising preparing the compound represented by Formula 3 by generating a ketone group through hydration and oxidation.

9. A method of manufacturing a compound, the method comprising:

reacting the compound represented by Formula 5 with benzaldehyde, and halogenating the reacted compound to form a first mixture;

reacting the first mixture with an organic metal compound in an organic solvent to form a second mixture; and reacting the second mixture under an acid catalyst to form a compound represented by Formula 1:

[Formula 5]

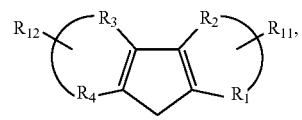

[Formula 1]

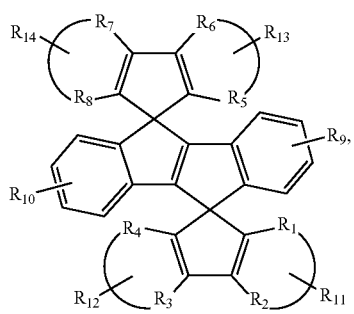

wherein each of $R_1$ and $R_2$, $R_3$ and $R_4$, $R_5$ and $R_6$, and $R_7$ and $R_8$ independently represents a 5 or 6-membered cyclic and $R_9$, $R_{10}$, $R_{11}$, $R_{12}$, $R_{13}$, and $R_{14}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl —$N(Z_1)(Z_2)$, or —$Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group, or wherein each of $R_1$, $R_2$, $R_3$, $R_4$, $R_5$, $R_6$, $R_7$, and $R_8$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —$N(Z_1)(Z_2)$, or —$Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

10. An organic light emitting device, comprising:

an anode disposed on a substrate;

a hole transport layer disposed on the anode;

an emission layer disposed on the hole transport layer and comprising a compound represented by Formula 1;

an electron transport layer disposed on the emission layer; and a cathode disposed on the electron transport layer:

[Formula 1]

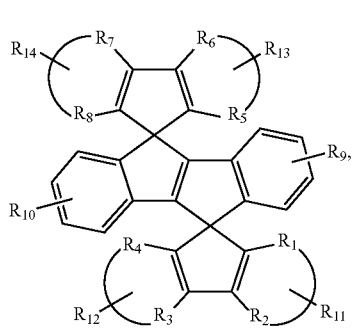

wherein each of $R_1$ and $R_2$, $R_3$ and $R_4$, $R_5$ and $R_6$, and $R_7$ and $R_8$ independently represents a 5 or 6-membered cyclic and $R_9$, $R_{10}$, $R_{11}$, $R_{12}$, $R_{13}$, and $R_{14}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —$N(Z_1)(Z_2)$, or —$Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group, or wherein each of $R_1$, $R_2$, $R_3$, $R_4$, $R_5$, $R_6$, $R_7$, and $R_8$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, —$N(Z_1)(Z_2)$, or —$Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

11. The organic light emitting device of claim 10, wherein the compound represented by Formula 1 is a host of the emission layer, or a dopant of the emission layer.

12. The organic light emitting device of claim 10, wherein the hole transport layer or the electron transport layer comprises the compound represented by Formula 1.

13. The organic light emitting device of claim 10, further comprising a hole injecting layer disposed between the anode and the hole transport layer.

14. The organic light emitting device of claim 13, wherein the hole injecting layer comprises the compound represented by Formula 1.

15. The organic light emitting device of claim 10, further comprising an electron injecting layer disposed between the electron transport layer and the cathode.

16. The organic light emitting device of claim 15, wherein the electron injecting layer comprises the compound represented by Formula 1.

17. The organic light emitting device of claim 15, further comprising a hole blocking layer disposed between the emission layer and the electron injecting layer.

18. The organic light emitting device of claim 17, wherein the hole blocking layer comprises the compound represented by Formula 1.

19. An organic light emitting display, comprising:
a first signal line and a second signal line crossing each other;
a switching thin film transistor connected to the first signal line and the second signal line;
a driving thin film transistor connected to the switching thin film transistor;
an organic layer covering the first signal line, the second signal line, the switching thin film transistor, and the driving thin film transistor;
a pixel electrode disposed on the organic layer, the pixel electrode connected to the driving thin film transistor;
a pixel defining layer disposed on the organic layer, the pixel defining layer surrounding the pixel electrode;
a light emitting member disposed on the pixel electrode, the light emitting member comprising a compound represented by Formula 1; and
a common electrode disposed on the light emitting member:

[Formula 1]

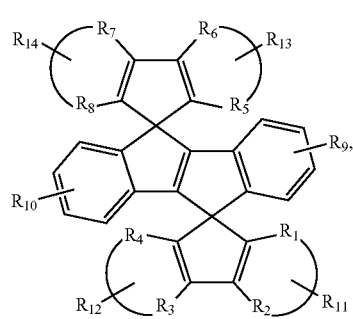

wherein each of $R_1$ and $R_2$, $R_3$ and $R_4$, $R_5$ and $R_6$, and $R_7$ and $R_8$ independently represents a 5 or 6-membered cyclic and $R_9$, $R_{10}$, $R_{11}$, $R_{12}$, $R_{13}$, and $R_{14}$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, $-N(Z_1)(Z_2)$, or $-Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group, or wherein each of $R_1$, $R_2$, $R_3$, $R_4$, $R_5$, $R_6$, $R_7$, and $R_8$ represents hydrogen, a substituted or non-substituted C1-C50 alkyl group, a substituted or non-substituted C1-C50 alkoxy group, a substituted or non-substituted C6-C50 aryl group, a substituted or non-substituted C2-C50 heteroaryl group, a substituted or non-substituted C5-C50 cycloalkyl group, a substituted or non-substituted C5-C30 heterocycloalkyl group, $-N(Z_1)(Z_2)$, or $-Si(Z_3)(Z_4)(Z_5)$, where each of $Z_1$, $Z_2$, $Z_3$, $Z_4$, and $Z_5$ independently represents hydrogen, a substituted or non-substituted C6-C30 aryl group, a substituted or non-substituted C2-C30 heteroaryl group, a substituted or non-substituted C5-C20 cycloalkyl group, or a substituted or non-substituted C5-C30 heterocycloalkyl group.

20. The organic light emitting display of claim 19, wherein the light emitting member comprises at least one of an emission layer, an electron transport layer, an electron injecting layer, a hole transport layer, a hole injecting layer, and a hole blocking layer.

21. The organic light emitting display of claim 20, wherein the compound represented by Formula 1 is a host of the emission layer, or a dopant of the emission layer.

* * * * *